United States Patent [19]

Kayane et al.

[11] Patent Number: 5,244,651

[45] Date of Patent: Sep. 14, 1993

[54] METHOD OF DESENSITIZING HYPERSENSITIVE DENTIN

[75] Inventors: Shigeto Kayane, Wakayama; Katsumi Kita, Izumisano; Ryozo Nakai; Yoshiaki Fujikura, both of Utsunomiya; Yasuteru Eguchi, Tokyo, all of Japan

[73] Assignee: Kao Corporation, Tokyo, Japan

[21] Appl. No.: 941,242

[22] Filed: Sep. 4, 1992

[30] Foreign Application Priority Data

Sep. 4, 1991 [JP] Japan .................................. 3-224190
Sep. 10, 1991 [JP] Japan .................................. 3-230598
Oct. 14, 1991 [JP] Japan .................................. 3-264919

[51] Int. Cl.$^5$ ...................... A61K 7/16; A61K 33/06; A61K 33/30
[52] U.S. Cl. ........................................ 424/42; 424/57; 424/641; 424/642; 424/685
[58] Field of Search ...................................... 424/49-58, 424/641, 642, 685

[56] References Cited

U.S. PATENT DOCUMENTS

| | | |
|---|---|---|
| 3,689,636 | 9/1972 | Svajda . |
| 4,177,258 | 12/1979 | Gaffar et al. ........................... 424/49 |
| 4,183,915 | 1/1980 | Gaffar et al. ........................... 424/49 |
| 4,348,381 | 9/1982 | Gaffar et al. ........................... 424/49 |
| 4,726,943 | 2/1988 | Klueppel et al. ...................... 424/49 |
| 4,892,724 | 1/1990 | Amjad ................................... 424/49 |
| 5,049,375 | 9/1991 | Tsujita et al. ........................... 424/52 |
| 5,130,146 | 7/1992 | Tsujita et al. ........................... 424/52 |

FOREIGN PATENT DOCUMENTS

| | | |
|---|---|---|
| 400641 | 12/1990 | European Pat. Off. . |
| 3-007214 | 1/1991 | Japan . |
| 4-217617 | 8/1992 | Japan . |
| 4-217618 | 8/1992 | Japan . |
| 4-221307 | 8/1992 | Japan . |
| 4-275213 | 9/1992 | Japan . |
| 2239601 | 7/1991 | United Kingdom . |

OTHER PUBLICATIONS

Tanizawa et al CA 114:115044g (1990).
Addy et al CA 110: 205644z (1988).
Dowell et al CA 102: 17616c (1984).
Shinozaki et al CA 118: 66629y (1992).
Okajima et al CA 117: 239514s (1992).
Shinozaki et al CA 117: 239513r (1992).
Okajima et all CA 117: 239512q (1992).
Tsujita et al CA 115: 99027s (1991).
Tsujita et al CA 115: 99024p (1990).
J. Periodontol, vol. 55, Dec. 1984; pp. 720-724, J. F. Collins, et al., "Clinical Evaluation of the Effectiveness of Three Dentifrices in Relieving Dentin Sensitivity".

*Primary Examiner*—Shep K. Rose
*Attorney, Agent, or Firm*—Oblon, Spivak, McClelland, Maier & Neustadt

[57] ABSTRACT

A method of desensitizing hypersensitive dentin is disclosed. The method comprises treating teeth of patients suffering from hypersensitive dentin with a colloid produced by mixing (a) a salt of polyvalent metal and (b) a polyol phosphate and/or a water-soluble salt thereof. The colloid can constrict or occlude dentinal tubules in the tooth dentin, exhibiting a continuous effect on the desensitization of hypersensitive dentin owing to the very high absorptivity of the colloid to teeth. The colloid does not impair taste, and does not produce precipitate near the neutral region, enabling it to be used safely.

7 Claims, No Drawings

METHOD OF DESENSITIZING HYPERSENSITIVE DENTIN

BACKGROUND OF THE INVENTION

1. Field of the Invention

The present invention relates to a method of desensitizing hypersensitive dentin, and, more particularly, to a method of desensitizing hypersensitive dentin by continuously constricting or occluding the dentinal tubules in the tooth dentin.

2. Background Art

Hypersensitive dentin symptom is a malady accompanied by pain in the dentin which has been exposed due to various reasons and is stimulated by cold water, rubbing, or the like. In recent years, along with the progress of prolongation of life-span, an increasing number of people are suffering from gingiva degeneration and paradentitis. The trend magnifies the clinical significance of hypersensitive dentin. The hydraulic dynamism theory is currently predominant as the cause of hypersensitive dentin. According to this theory, the stimuli conveyed through dentinal tubules irritates nerves distributed over dental pulp and tooth dentin, causing a pain in these areas. Suppressing hypersensitive dentin and ameliorating or alleviating the pain are considered to be achieved by sealing dentinal tubules which is the consciousness conductor by physical or chemical means, or by fixing the dentinal tubules with proteins.

Therapeutic means for desinsitizing hypersensitive dentin have been reported by J. F. Collins et al [J. Periodontol, 55, 720 (1984)] relating to dentifrices containing sodium citrate and U.S. Pat. No. 3,689,636 relating to compositions containing a water-soluble chloride such as calcium chloride, magnesium chloride, and potassium chloride.

The above therapeutic means using water-soluble metal ions, however, have drawbacks in that (1) the effects do not last long, (2) the chemicals irritate to dental pulp, (3) the chemicals produce unfavorable taste, (4) the chemicals cannot be used in conditions at near-neutral levels because precipitation of hydroxides occurs, and the like.

In view of this situation, the present inventors have undertaken extensive studies in order to develop a method of desensitizing hypersensitive dentin which is free from the above-described drawbacks (1)–(4). As a result, the present inventors have found that application of a colloid produced by mixing a polyvalent metal salt and a polyol phosphate in an aqueous medium to teeth can continuously constrict or occlude dentinal tubules in the tooth dentin, without complications, such as production of precipitates in the neighborhood of neutral, and the like. This finding has led to the completion of the present invention.

SUMMARY OF THE INVENTION

Accordingly, an object of the present invention is to provide a method of desensitizing hypersensitive dentin comprising treating teeth of patients suffering from hypersensitive dentin with a colloid produced by mixing (a) a salt of polyvalent metal and (b) a polyol phosphate and/or a water-soluble salt thereof, in an acidic or neutral aqueous medium. After mixing, the aqueous solution may be adjusted to pH of around neutral.

Another object of the present invention is to provide a method of desensitizing hypersensitive dentin comprising treating teeth of patients suffering from hypersensitive dentin with a composition which comprises a colloid at a concentration of 10–100,000 ppm, as metal, produced by mixing (a) a salt of polyvalent metal and (b) a polyol phosphate and/or a water-soluble salt thereof, in an acidic or neutral aqueous medium. After mixing, the aqueous solution may be adjusted to pH of around neutral.

Other objects, features and advantages of the invention will hereinafter become more readily apparent from the following description.

DETAILED DESCRIPTION OF THE INVENTION AND PREFERRED EMBODIMENTS

The colloids used in the desensitizing method of the present invention can be obtained by mixing said component (a) and component (b) in an acidic or neutral aqueous medium. The aqueous medium may be adjusted to pH of around neutral.

There are no specific restrictions as to a polyvalent metal salt which is component (a) of the colloid of the present invention, so long as its hydroxide is insoluble or hardly soluble in water. Examples of such metal salts include chlorides, sulfates, nitrates, and the like of alkaline earth metal, e.g., Mg, Sr, Ba; and other metals such as Zn, Fe, Ti, Al, Cr, Mn, Cu, Ni, Co, Bi, Sn, V, Mo, Nb, Zr, Sb, In, lanthanoids, or the like. Among them, salts of Zn, Fe, Ti, Al, Sn, Cu, Ni, Mg, Ba, Sr, V, Mn, Mo, Nb, Zr, Sb, In, or lanthanoids are preferable, and especially preferred are salts of Zn, Fe, Ti, Al, Sn, Mg, Sr, or Mn.

These polyvalent metal salts are used upon dissolving them in the form of chloride, sulfate or nitrate into an acidic or neutral aqeous solution.

Given as specific examples of component (a), by way of salts of zinc, are zinc chloride, zinc bromide, zinc sulfate, zinc nitrate, zinc acetate, zinc lactate, zinc aspartate, zinc citrate, and the like.

The above metal salts may be used either individually or in combination of two or more. Such examples may include metal salts other than zinc salt.

Phosphates of monosaccharide, oligosaccharide, polysaccharide, or polyol are given as examples of another component, component (b). Specific examples include glucose-1-phosphate, glucose-6-phosphate, mannose-6-phosphate, galactose-6-phosphate, fructose-6-phosphate, glucose-1,6-diphosphate, fructose-1,6-diphosphate, α-glycerophosphate, β-glycerophosphate, sucrose phosphate, ascorbic acid phosphate, sorbitol phosphate, phosphorilated polyglycerine, phosphorilated polyethylene glycol, phosphorilated starch, and the like. Water-soluble salts of these polyol phosphates may be salts of alkali metal, alkaline earth metal, amine, amino acid, or the like. Of the above compounds, glucose-1-phosphate, glucose-6-phosphate, fructose-6-phosphate, fructose-1,6-diphosphate, α-glycerophosphate, β-glycerophosphate, ascorbic acid phosphate, sucrose phosphate, sorbitol phosphate, and phosphorilated polyethylene glycol, as well as their salts are preferable.

The colloids used in the present invention can be prepared by mixing the above components (a) and (b) in an aqueous medium in an acidic or neutral aqueous medium. The aqueous medium may be adjusted to pH of around neutral. Water is an especially preferable aqueous medium used for this purpose, and may be used along with an organic solvent such as alcohol unless it works adversely to the reaction. There are no specific limitations as to the method by which components (a) and (b) are mixed. For example, component (a) may be added to an aqueous solution of component (b) and mixed, component (b) may be added to an aqueous solution of component (a) and mixed, or an aqueous solution of component (a) and an aqueous solution of component (b), separately prepared, may be mixed together.

There are no specific limitations as to the ratio of components (a) and (b) to be mixed. An amount of component (b) of 0.5 mol or more, preferably 1 mol or more, of component (a) is applicable. It is desirable that the solution prepared by mixing components (a) and (b) have a pH of preferably 3–10, and particularly preferably 6–8. The target colloid cannot be obtained if the pH is less than 3; at pH 10 or more, it is difficult to obtain a stable colloid because colloidal particles tend to agglomerate at higher pHs. The pH of the solutions can be adjusted by using a suitable acid or base. Temperature and other mixing conditions are suitably determined without any specific limitations.

Colloids thus obtained can be isolated by means of supercentrifuge, freeze-dry, or the like. These colloids can be reused by dispersing them again into water. The resulting colloid particles have a diameter, usually, of 1–500 nm.

Colloids produced by the above-described method are metal hydroxide compound colloids which are insoluble or hardly soluble in water. Although particulars of the colloid formation reaction are not completely elucidated, it is assumed that the metal salt of component (a) is first hydrolyzed by the aqueous medium into the hydroxide compound, and then an insoluble hydroxide compound incurs certain action from component (b) to produce a stable colloid.

In the present invention, "insoluble" means that a compound is substantially insoluble in water, and "hardly soluble" means that the solubility of a compound at 25° C. is 10% by weight or smaller.

In order to treat the teeth of hypersensitive dentin patients with the colloid thus obtained, a composition comprising the colloid solution may be applied to the teeth, or the patients may gargle or brush their teeth with such a composition.

The colloid is incorporated into the composition of the present invention at a concentration of 10–100,000 ppm, preferably 10–50,000 ppm, as metal.

Various known components may be incorporated into the composition of the present invention according to the use to which it is directed. Such components may include, moisturizing agents, antiseptics, enzymes, perfumes, surfactants, and the like.

There are no specific limitations to the form of the composition of the present invention; it may be a dentifrice, tooth-coating agent, mouthwash, buccal tablet, chewing gum, or the like. They can be prepared by methods conventionally employed in the preparation of these forms of compositions.

According to the desensitizing method of the present invention, the colloid can constrict or occlude dentinal tubules in the tooth dentin. A continuous hypersensitive dentin therapeutic action is effectively exhibited owing to the adsorption of the colloid on teeth. The colloid does not impair taste, and does not produce precipitate near the neutral region, allowing it to be used safely.

Other features of the invention will become apparent in the course of the following description of the exemplary embodiments which are given for illustration of the invention and are not intended to be limiting thereof.

EXAMPLES

EXAMPLE 1

Glucose-1-phosphate was used as the polyol phosphate. First, 5.7 g (15 mmol) of disodium salt of glucose-1-phosphate (tetra-hydrate) was dissolved into 50 ml of ion-exchanged water. 1.0 g (7.3 mmol) of zinc chloride was added to the solution and mixed. After adjusting the pH to 7.5 with 1N sodium hydroxide solution, ion exchanged water was added to make the volume of the solution 100 ml, thus producing an aqueous solution of zinc colloid (5,000 ppm as Zn).

Similar colloidal solutions (5,000 ppm as Zn) were prepared by using, instead of the disodium salt of glucose-1-phosphate, sodium salt of glucose-6-phosphate, glycerophosphate, fructose-1,6-diphosphate, sucrose phosphate, and phosphorilated polyethylene glycol.

Tooth specimens prepared from dental carvix of a freshly extracted tooth, of which the dentinal tubules were exposed by abrasion and a phosphoric acid treatment, were immersed in 10 ml of each of the aqeuos solutions of zinc colloid for 5 minutes. The tooth specimens were than washed with the same amount of ion exchanged water, dried, and submitted to investigation by a scanning electron microscope to confirm that all colloidal solutions exhibited the effect of constricting or occluding dentinal tubules.

EXAMPLE 2

Disodium salt of glucose-1-phosphate (tetra-hydrate) was used as the polyol phosphate. 13.9 g (0.015 mol) of this compound was dissolved into 60 ml of ion-exchanged water. 4.5 g (0.005 mmol) of aluminum chloride (hexa-hydrate) was added to the solution and mixed. After adjusting the pH to 7 with 1N sodium hydroxide solution, ion exchanged water was added to make the volume of the solution 100 ml, thus producing a colloidal solution (5,000 ppm as Al).

Tooth specimens prepared from dental carvix of a freshly extracted tooth, of which the dentinal tubules were exposed by abrasion and a phosphoric acid treatment, were immersed in 10 ml of the colloidal solution for 5 minutes. The tooth specimens were than washed with 10 ml ion exchanged water, dried, and submitted to investigation by a scanning electron microscope to confirm that the dentinal tubules were constricted or occluded.

Similar colloidal solutions were prepared by using chlorides of Ti, Sn, Sr, Fe, Mg, and Mn, instead of aluminum chloride. The same tooth specimens as above were dipped into these solutions to confirm that the same effects as above resulted.

EXAMPLE 3

Colloidal solutions (metal content: 5,000 ppm) of pH 7 were prepared in the same manner as in Example 2, by using, as a polyol phosphate, sodium salt of glucose-6-phosphate, glycerophosphate, fructose-1,6-diphosphate, sucrose phosphate, and phosphorilated polyethylene glycol.

In the same manner as in Example 1, the tooth specimens were dipped into these solutions for 5 minutes. All colloidal solutions were confirmed to constrict or occlude the dentinal tubules.

EXAMPLE 4

Six aqueous solutions of zinc colloid of pH 7.5 (zinc content: 21,000 ppm) were prepared in the same manner as in Example 1, and were absorbed into sponges. The solutions were lightly coated onto surfaces of tooth dentin of patients suffering from hypersensitive dentin using the sponges. All solutions were confirmed to reduce the symptom of hypersensitive dentin and to continuously maintain the effect for longer than 1 month.

EXAMPLE 5

A colloidal solution was prepared in the same manner as in Example 2 from aluminum chloride and glucose-1-phosphate (5,000 ppm as Al). The solutions were coated onto surfaces of tooth dentin of patients suffering from hypersensitive dentin using the same type of sponge treated in the same manner as in Example 4 to confirm that the colloidal solution reduced the sympton of hypersensitive dentin.

EXAMPLE 6

Six colloidal solutions of pH 7.5 (zinc content: 5,000 ppm), 20 ml each, were submitted to gargling for 30 seconds by patients suffering from hypersensitive dentin to confirm that all solutions can reduce the symptom of hypersensitive dentin.

EXAMPLE 7

Adsorption capability of colloids on hydroxyapatite (HAP) was examined. 1 g of hydroxyapatite was dipped into 50 ml of zinc colloidal solutions (pH 7.5, Zn concentration 65 mM) prepared in Example 1 or aluminum colloidal solutions (pH 7.5, Al concentration 65 mM) prepared in Example 2, stirred at 30° C. for 12 hours, washed with water, and dried to measure amounts of metals adsorbed on the surface of hydroxyapatite. As a result, the adsorption capability of zinc type colloids was found to be 0.67 mmol/g-HAP and that of aluminum type colloids 0.35 mmol/g-HAP, indicating that both have a high adsorption capability.

EXAMPLE 8

The effectiveness of the method of the present invention was examined by applying a colloid therapy to patients suffering from hypersensitive dentin.

Colloidal solutions (metal concentration: 20,000 ppm) were directly applied to affected teeth of patients, followed by drying by air gun. The procedure of application and drying was repeated several times as needed.

The affected potions were stimulated by air gun and the patients were questioned to answer with regard to the extent of pain in 5 grades. The rate of reduction in the degree of pain was calculated from the answers the patients gave (in 5 grades) prior to and after the application. The results, grouped into four classes of very effective, effective, ineffective, and exacerbation, are shown in Table 1, which indicates 67% or more effectiveness for all colloids.

TABLE 1

|  | Zn Colloid | Sr Colloid | Sn Colloid |
| --- | --- | --- | --- |
| Very effective | 6 | 1 | 3 |
| Effective | 20 | 20 | 17 |
| Ineffective | 4 | 9 | 10 |
| Exacerbation | 0 | 0 | 0 |
| Total | 30 | 30 | 30 |
| Effectiveness (%) | 87 | 70 | 67 |

EXAMPLE 9

A colloid was prepared in the same manner as in Example 1 by mixing aluminum chloride or zinc chloride and sodium glucose-1-phosphate in water. Other components were deaerated and mixed to obtain a tooth paste composition with the formulation shown below.

The action of this composition on the constriction or occlusion of dentinal tubules was evaluated by means of SEM to confirm a superior effect.

| <Formulation> | (% by weight) |
| --- | --- |
| Colloid | 6.0 |
| Sodium hydrogen carbonate | 0.2 |
| Aluminum hydroxide | 35.0 |
| Hydroxyethyl cellulose | 2.0 |
| Sucrose fatty acid ester | 2.5 |
| Fatty acid diethanolamide | 0.5 |
| Glycerine | 10.0 |
| 70% Sorbit solution | 15.0 |
| Methyl paraben | 0.1 |
| Perfume | 1.0 |
| Saccharin sodium | 0.2 |
| Total | 100.0 |

EXAMPLE 10

A colloid was prepared in the same manner as in Example 1 by mixing aluminum chloride or zinc chloride and sodium glucose-1-phosphate in water. Other components were deaerated and mixed to obtain a mouthwash composition with the formulation shown below.

The action of this composition on the constriction or occlusion of dentinal tubules was evaluated by means of SEM to confirm a superior effect.

| <Formulation> | (% by weight) |
| --- | --- |
| Colloid | 4.0 |
| Sodium hydrogen carbonate | 0.2 |
| Glycerine | 5.0 |
| Polyoxyethylene hydrogenated castor oil | 0.5 |
| Ethanol | 8.0 |
| Saccharin sodium | 0.1 |
| Perfume | 0.1 |
| Coloring agent | q.s. |
| Water | q.s. |
| Total | 100.0 |

Obviously, numerous modifications and variations of the present invention are possible in light of the above teachings. It is therefore to be understood that within the scope of the appended claims, the invention may be practiced otherwise than as specifically described herein.

What is claimed is:

1. A method of desensitizing hypersensitive dentin comprising treating teeth of patients suffering from hypersensitive dentin with a colloid produced by mixing (a) a salt of polyvalent metal and (b) a polyol phosphate and/or a water-soluble salt thereof, in an aqueous medium.

2. The method according to claim 1, wherein said component (a) is a salt of metal selected from the group consisting of Zn, Fe, Ti, Al, Sn, Cu, Ni, Mg, Ba, Sr, V, Mn, Mo, Nb, Zr, Sb, In, and lanthanoid.

3. The method according to claim 1, wherein said component (b) is one or more compounds selected from the group consisting of glucose-1-phosphate, glucose-6-phosphate, mannose-6-phosphate, galactose-6-phosphate, fructose-6-phosphate, glucose-1,6-diphosphate, fructose-1,6-diphosphate, α-glycerophosphate, β-glycerophosphate, sucrose phosphate, ascorbic acid phosphate, sorbitol phosphate, phosphorilated polyglycerine, phosphorilated polyethylene glycol, and their water-soluble salts.

4. A method of desensitizing hypersensitive dentin comprising treating teeth of patients suffering from hypersensitive dentin with a composition which comprises a colloid at a concentration of 10–100,000 ppm, as metal, produced by mixing (a) a salt of polyvalent metal and (b) a polyol phosphate and/or a water-soluble salt thereof, in an aqueous medium.

5. The method according to claim 4, wherein said component (a) is a salt of metal selected from the group consisting of Zn, Fe, Ti, Al, Sn, Cu, Ni, Mg, Ba, Sr, V, Mn, Mo, Nb, Zr, Sb, In, and lanthanoid.

6. The method according to claim 4, wherein said component (b) is one or more compounds selected from the group consisting of glucose-1-phosphate, glucose-6-phosphate, mannose-6-phosphate, galactose-6-phosphate, fructose-6-phosphate, glucose-1,6-diphosphate, fructose-1,6-diphosphate, α-glycerophosphate, β-glycerophosphate, sucrose phosphate, ascorbic acid phosphate, sorbitol phosphate, phosphorilated polyglycerine, phosphorilated polyethylene glycol, and their water-soluble salts.

7. The method according to claim 4, wherein said treating of teeth with said composition is performed by coating of said composition on the teeth, by brushing teeth, or by gargling using said composition.

* * * * *